United States Patent [19]
Cox et al.

[11] 4,288,234
[45] Sep. 8, 1981

[54] RECOVERY OF AROMATICS FROM STYRENE PRODUCTION OFF-GAS

[75] Inventors: Robert P. Cox, Wyckoff, N.J.; Norbert R. Tarradellas, Basrah, Iraq

[73] Assignee: The Lummus Company, Bloomfield, N.J.

[21] Appl. No.: 94,672

[22] Filed: Nov. 15, 1979

[51] Int. Cl.³ ............................................. B01D 47/00
[52] U.S. Cl. .......................................... 55/48; 55/50; 55/53; 55/89; 585/805; 585/867
[58] Field of Search .................. 55/23, 24, 36, 46–51, 55/53, 84, 89; 585/805, 833–835, 838, 867

[56] References Cited

U.S. PATENT DOCUMENTS

| | | | |
|---|---|---|---|
| 2,729,588 | 1/1956 | Hannah | 55/46 |
| 2,959,626 | 11/1960 | Krausse et al. | 585/805 |
| 3,412,171 | 11/1968 | Welch et al. | 585/838 |

FOREIGN PATENT DOCUMENTS

| | | | |
|---|---|---|---|
| 49-20186 | 5/1974 | Japan | 585/867 |
| 49-20188 | 5/1974 | Japan | 585/805 |

*Primary Examiner*—Bernard Nozick
*Attorney, Agent, or Firm*—Louis E. Marn; Elliot M. Olstein

[57] ABSTRACT

An off-gas from a process for producing styrene from ethylbenzene, which contains non-condensables; in particular, hydrogen, as well as some aromatics; in particular, ethylbenzene, is contacted with a higher boiling absorption oil to scrub aromatics from the off-gas and provide an off-gas essentially free of aromatics. The absorption step is employed as a final treatment of the off-gas; i.e., subsequent to initial treatment of the off-gas by chilling and/or ethylbenzene scrubbing to initially reduce the aromatics content thereof. A preferred absorption oil is the heavy byproducts obtained from a process for producing ethylbenzene, which contains polyethylbenzenes.

5 Claims, 3 Drawing Figures

RECOVERY OF AROMATICS FROM STYRENE PRODUCTION OFF-GAS

This invention relates to the production of styrene, and more particularly to treating an off-gas produced in a process directed to the production of styrene from ethylbenzene.

In the catalytic dehydrogenation of ethylbenzene to produce styrene, the reactor effluent is normally cooled and partially condensed to recover crude styrene product. The off-gas from the cooling and partial condensation, which contains primarily hydrogen as the noncondensable, has a high content of aromatic hydrocarbons. In order to reduce such aromatic hydrocarbon losses, such off-gas is generally compressed, partially condensed and scrubbed with ethylbenzene, followed by cooling and chilling to thereby reduce the aromatic content. In such processes, however, the vapors, which contain as major components hydrogen, methane and carbon dioxide, are saturated with water and aromatic hydrocarbons; namely, ethylbenzene. Such aromatics represents an important loss of feedstock.

The present invention is directed to treating the off-gas from a process directed to producing styrene from ethylbenzene in order to provide an off-gas essentially free of aromatic hydrocarbons.

In accordance with the present invention, the off-gas from the process for producing styrene from ethylbenzene is finally treated with a heavier oil which absorbs aromatics to thereby provide a remaining off-gas which is essentially free of aromatic hydrocarbons.

The oil for absorbing aromatic hydrocarbons generally has a 5-volume percent distillation temperature of at least 400° F., with the 5-volume percent distillation temperature generally being at least 600° F. In most cases, the 95-volume percent distillation temperature does not exceed about 1000° F. The absorption oil may be any one of a wide variety of absorption oils which are known to be effective for absorbing aromatics such as ethylbenzene, with such absorption oil being characterized by the 5-volume percent boiling characteristics hereinabove noted. In most cases, the absorption oils which are effective for absorbing aromatics are of an aromatic nature, although such absorption oils may contain some aliphatic components. As representative examples of suitable absorption oils, there may be mentioned gas oils, fluid catalytic cracking cycle oils, lube oil extraction raffinates and the like. A preferred absorption oil is the heavy byproduct from the process for producing ethylbenzene by alkylation of benzene. Such heavy byproduct generally contains as principal components polyethylbenzenes and diphenylethane.

The off-gas which is subjected to scrubbing with the heavier absorption oil generally has an aromatics content of from 0.5 to about 10-volume percent, with the other principal components being hydrogen, methane, water vapor and carbon dioxide. The aromatics present in the off-gas are principally comprised of ethylbenzene and the off-gas may further include one or more of benzene, toluene and styrene.

The scrubbing with the heavier absorption oil is employed as a final treatment of the off-gas in order to essentially eliminate aromatics therefrom. Consequently, prior to contact with the heavier absorption oil, the off-gas has been treated to reduce the aromatic content thereof by one or more of chilling and/or ethylbenzene scrubbing.

The invention will be further described with respect to preferred embodiments thereof illustrated in the accompanying drawings, wherein.

It is to be understood, however, that the scope of the invention is not to be limited by the preferred embodiments disclosed with reference to the accompanying drawings.

Figure 1:
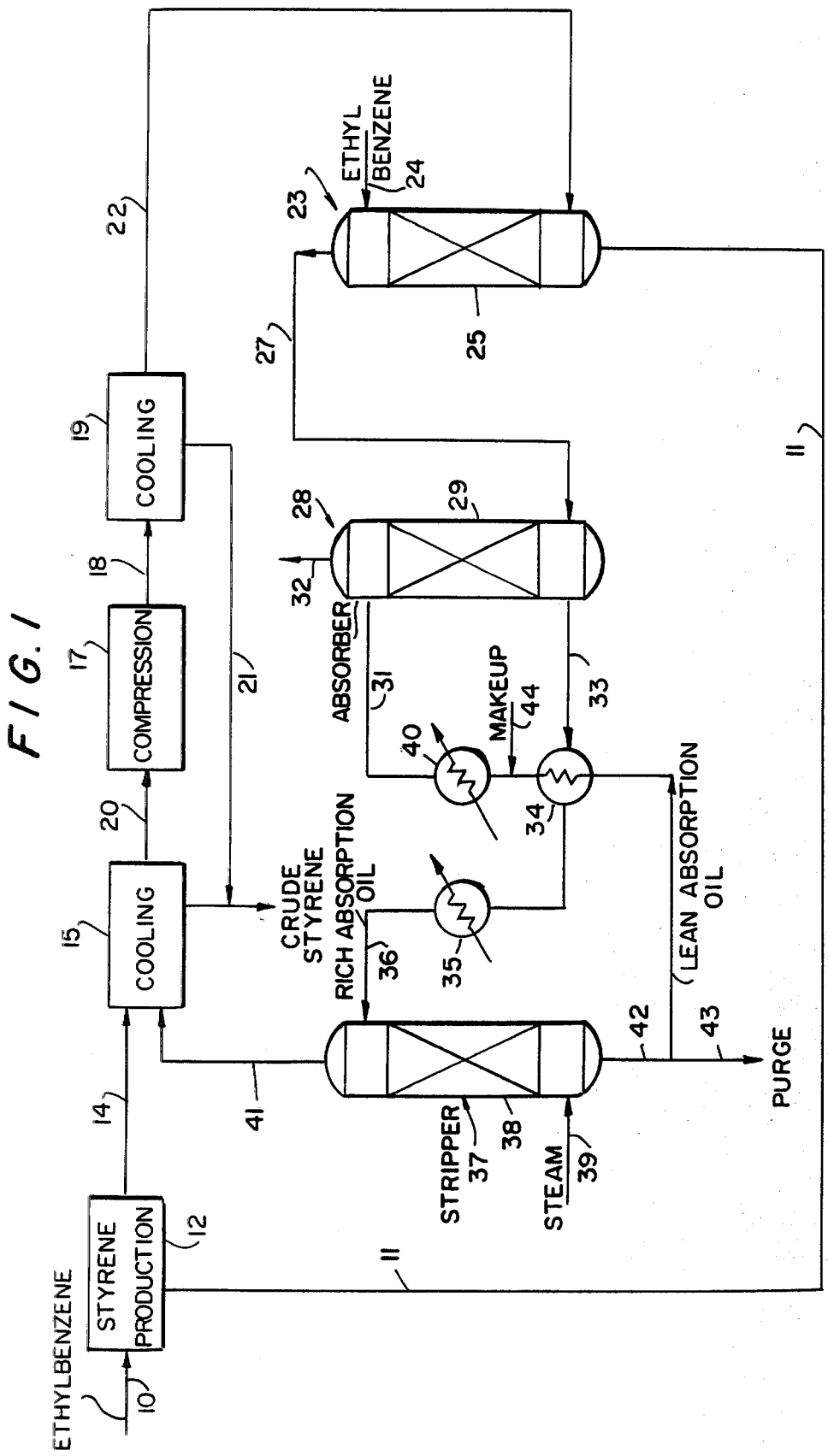
FIG. 1 is a simplified schematic flow diagram of a preferred embodiment of the present invention.

Referring now to FIG. 1 of the drawings, ethylbenzene fresh feed, in line 10, and a further portion of ethylbenzene fresh feed, including absorbed aromatics, in line 11, obtained as hereinafter described, are introduced into a styrene production zone, generally designated as 12 wherein the ethylbenzene is catalytically dehydrogenated to produce styrene, by a procedure known in the art. As known in the art, the feed to zone 12 generally also includes steam. In general, the styrene production is operated at a temperature in the order of from 500° F. to 1500° F., and at a pressure in the order of from 2 to 25 psia.

A styrene production effluent is withdrawn from the styrene production zone 12 through line 14 and introduced into a suitable cooling zone, schematically generally indicated as 15 (which may contain one or more cooling stages) in order to cool the effluent gas and condense crude styrene product, which contains in addition to styrene, ethylbenzene, and one or more of toluene and benzene. Crude styrene product is withdrawn from cooling zone 15, through line 16 for introduction into a separation and recovery zone (not shown).

Uncondensed gas, which is at a temperature in the order of from 60° F. to 150° F., and at a pressure of from 2 to 25 psia, is withdrawn from cooling zone 15 through line 20, and such gas contains hydrogen, methane, carbon dioxide, as well as water vapor and aromatics, (ethylbenzene and some styrene and/or toluene and/or benzene). The gas in line 20 is compressed by the use of a compressor, schematically generally indicated as 17, and the compressed gas in line 18 is introduced into a cooling zone, schematically generally indicated as 19, which may contain one or more cooling stages in order to reduce the temperature of the gas and condense aromatics therefrom. Condensed aromatics are recovered from cooling zone 19 through line 21, and are combined with the crude product in line 16 for introduction into the styrene separation and recovery zone (not shown).

The remaining gas withdrawn from the cooling zone 19 through line 22, which is generally at a temperature in the order of from 75° F. to 125° F., and at a pressure in the order of from 15 to 100 psia and which still contains aromatics, is introduced into a scrubbing zone, generally indicated as 23, wherein the gas is countercurrently contacted with a portion of the ethylbenzene fresh feed to the styrene production, introduced through line 24. The scrubber 23 contains suitable means, in order to increase gas-liquid contact, e.g. packing 25, and as a result of such contact, further aromatics are scrubbed from the gas.

Ethylbenzene, containing absorbed aromatics, is withdrawn from scrubber 25 through line 11 for introduction into the styrene production zone 12.

The gas withdrawn from scrubber 23 through line 27 is generally at a temperature in the order of from 35° F. to 150° F., and a pressure in the order of from 15 to 100 psia. Such gas still contains some aromatics, and in general, as hereinabove described, the aromatic content of the gas is in the order of from 0.5% to 10%, by volume.

The gas in line 27 is introduced into a further scrubber 28, which includes suitable gas-liquid contacting means, shown as bed 29 wherein the gas is contacted with an absorption oil introduced through line 31. The absorption oil introduced through line 31 is a heavy oil of the type hereinabove described, which is effective for absorbing aromatic hydrocarbons from the gas introduced through line 27. As hereinabove described, the absorption oil is preferably the heavy by-product from a process for producing ethylbenzene, and is characterized by a 5-volume percent distillation temperature of at least 400° F., preferably at least 600° F., and a 95-volume percent distillation temperature of no greater than 1000° F.

The scrubber 28 is operated at conditions to remove essentially all of the aromatics present in the gas introduced through line 27; i.e., the aromatic content of the scrubbed gas is less than 0.5%, most generally less than 0.2% and preferably less than 0.05%, all by volume. In general, scrubber 28 is operated at a temperature in the order of from 35° F. to 125° F., and a pressure in the order of from 15 to 100 psia.

An off-gas, essentially free of aromatic hydrocarbons, which generally contains 90-volume percent or more of hydrogen, is recovered from scrubber 28 through line 32. Such off-gas may be burned, or in some cases, may be further treated to recover hydrogen therefrom.

Rich absorption oil withdrawn from scrubber 28 through line 33 is heated in exchangers 34 and 35 prior to being introduced through line 36 into an absorption oil stripper, schematically generally indicated as 37, with the stripper being provided with suitable gas-liquid contacting means, such as a bed 38.

Stripper 37 is operated at temperatures and pressures to strip absorbed aromatics from the absorption oil, with the stripper 37 preferably being operated by the use of a suitable stripping gas, such as steam, provided through line 39. Although steam is preferred, it is to be understood that stripping gases other than steam may also be employed. Thus, for example, instead of steam, there may be used: nitrogen, methane, carbon dioxide or the like. The stripping gas can be a combination of the above. It is also to be understood that the stripper may be operated without a stripping gas, although this is less preferred. Alternatively, the stripper may be replaced with a flash drum when higher boiling absorption oils are used.

In general, stripper 37 is operated at a temperature in the order of from 125° F. to 300° F., and at a pressure in the order of from 1 to 25 psia.

Stripped aromatic components are withdrawn from stripper 37 through line 41, and such stripped components are introduced into the cooling zone 15 to condense such aromatics for recovery with the crude product in line 16. It is to be understood that the stripped aromatics can be condensed in a separate zone, although condensation in zone 15 is preferred.

Lean absorption oil is withdrawn from stripper 37 through line 42, and a portion thereof is purged through line 43, with the remaining portions being cooled in exchanger 34, by indirect heat transfer with rich absorption oil, and further cooled in exchanger 40, prior to introduction into scrubber 28 through line 31. Suitable make-up absorption oil is provided through line 44.

Thus, in accordance with the embodiment, the off-gas from the styrene production, which still contains some aromatic hydrocarbons, is finally treated with a heavier absorption oil to recover such aromatic hydrocarbons for ultimate reuse in the process.

Figure 2:
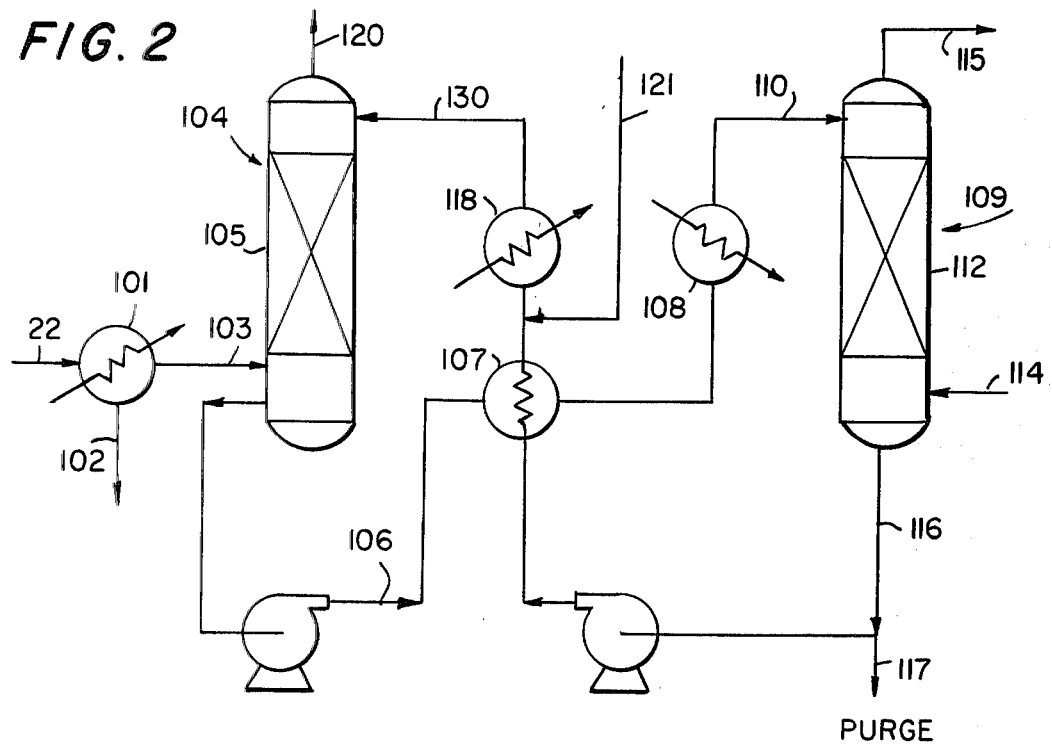
FIG. 2 is a simplified schematic flow diagram of a modification of the embodiment of FIG. 1.

Referring to FIG. 2 of the drawings, there is shown a modification of the embodiment described with respect to FIG. 1. Thus, in accordance with the embodiment of FIG. 2, off-gas from cooling stage 19, which is in line 22, is cooled in a chiller, schematically generally indicated as 101, to condense a portion of the aromatics contained therein, with the condensed portion being recovered in line 102 for introduction into the crude styrene recovery system (not shown), or in the alternative to the styrene production reactor.

The uncondensed portion of the gas, in line 103, which is generally at a temperature in the order of from 32° F. to 100° F., and at a pressure in the order of from about 15 to 100 psia is introduced into scrubber 104, including suitable gas-liquid contact means, in the form of a bed 105. In scrubber 104, the gas is contacted with a heavy absorption oil, of the type hereinabove described introduced through line 130 for absorbing aromatics which remain in the gas introduced through line 103. The scrubber 104 is operated at conditions to produce a gas which is essentially free of aromatics (as hereinabove described), with the essentially aromatics free gas, which primarily contains hydrogen and methane, being recovered through line 120 for further processing by burning or hydrogen recovery, as hereinabove described.

The scrubber 104 is generally operated at a temperature in the order of from 35° F. and 125° F., and at a pressure in the order of from 15 to 100 psia.

Rich absorption oil is withdrawn from scrubber 104 through line 106 and heated in exchangers 107 and 108 prior to introduction thereof into a stripping column 109 through line 110. The stripping column 109 is provided with suitable gas-liquid contact means, for example, a packed bed 112. The stripper 109 is provided with a suitable stripping gas, such as steam, through line 114; however, as hereinabove described with respect to the embodiment of FIG. 1, other stripping gases could be used, or in the alternative, the stripper could be operated without the use of a stripping gas or replaced with a flash drum. The stripper 109 is operated to strip absorbed aromatics from the absorption oil, with the stripped aromatics being withdrawn from stripper 109 through line 115 for introduction into the cooling zone 15, as hereinabove described with respect to the embodiment of FIG. 1, or in the alternative condensed separately. In general, the stripper is operated at a temperature in the order of from 125° F. to 300° F., and at a pressure in the order of 1 to 25 psia.

Lean absorption oil is withdrawn from stripper 109 through line 116, with a portion thereof being purged through line 117. Lean absorption oil is then cooled in exchanger 107 by indirect heat transfer with rich absorption oil, and further cooled in exchanger 118 prior to introduction into the scrubber 104. Make-up absorption oil is provided through line 121.

Thus, in accordance with the embodiment of FIG. 2, the ethylbenzene scrubber has been eliminated, and replaced by a chiller, with the off-gas being finally treated, as hereinabove described with respect to the embodiment of FIG. 1 by use of a heavier absorption oil in order to provide an off-gas which is essentially free of aromatics.

Figure 3:
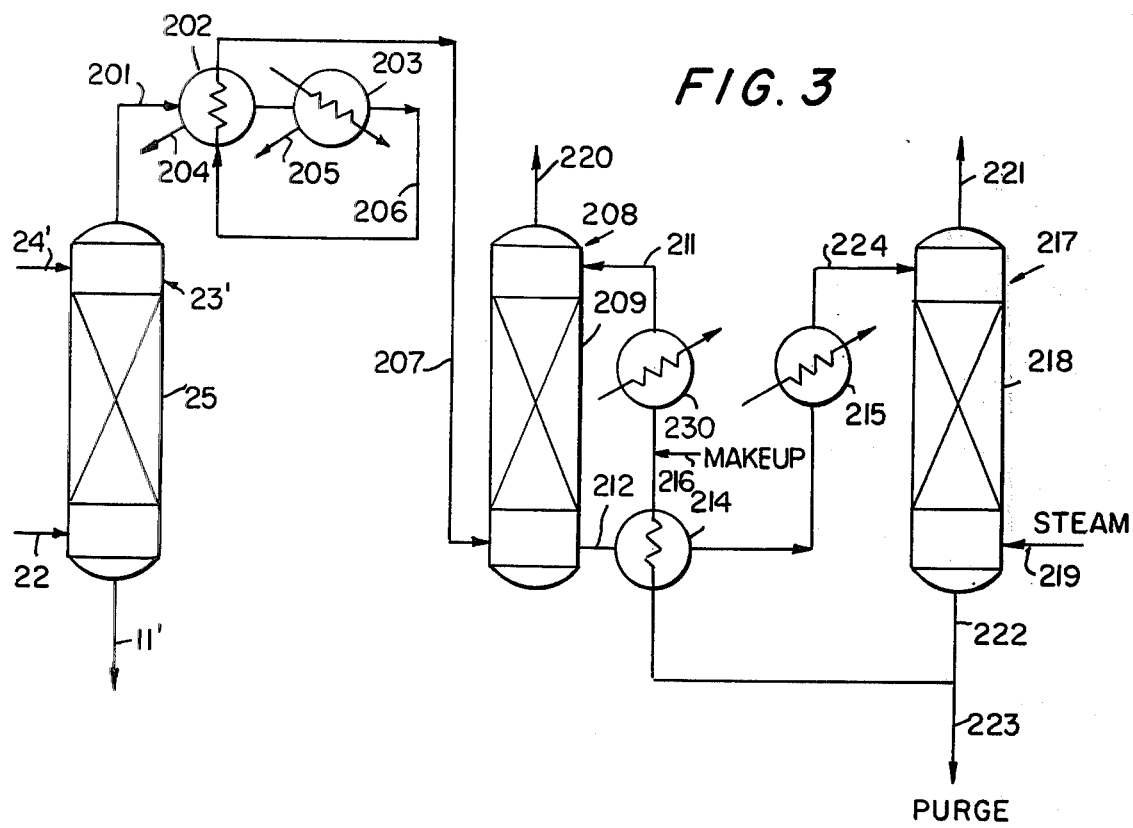
FIG. 3 is a simplified schematic flow diagram of a further modification of the embodiment of FIG. 1.

A further modification of the embodiment of FIG. 1 is shown in FIG. 3 of the drawings. Referring to FIG. 3, off-gas in line 22 is introduced into the ethylbenzene scrubber 23', which includes suitable gas-liquid contact bed 25', wherein the gas is countercurrently contacted with ethylbenzene, as an absorption liquid, introduced through line 24'. The scrubber 23' is operated as hereinabove described with respect to the embodiment of FIG. 1, with the ethylbenzene, containing absorbed aromatics being recovered therefrom through line 11' for recycle to the styrene production.

The gas withdrawn from scrubber 23' through line 201, which is generally at a temperature in the order of from 35° to 150° F. and a pressure in the order of from about 15 to 100 psia, is cooled in exchanger 202, and further chilled in chiller 203 in order to condense further aromatics from the gas, with the condensed aromatics being withdrawn from exchanger 202 through line 204 and from chiller 203 through line 205. The condensed aromatics recovered through lines 204 and 205 are recycled to the styrene production reactor or in the alternative to the recovery system. The gas withdrawn from chiller 203 through line 206, which is at a temperature in the order of from 32° F. to 100° F., and at a pressure in the order of from about 15 to 100 psia is heated in exchanger 202 by indirect heat transfer with the gas in line 201, and the heated gas in line 207 is introduced into an additional scrubber 208, which includes suitable gas-liquid contact means in the form of a bed 209 wherein the gas is countercurrently contacted with absorption oil introduced through line 211 for absorbing aromatics. The absorption oil employed in line 211 is a heavier absorption oil of the type hereinabove described. The scrubber 208 is operated at conditions to absorb essentially all of the aromatics present in the gas introduced through line 207, with a gas, essentially free of aromatics, as hereinabove described, being recovered from scrubber 208 through line 220 for burning and/or hydrogen recovery as hereinabove described. In general, the scrubber 208 is operated at temperature in the order of from 35° F. to 125° F., and at a pressure in the order of from 15 to 100 psia.

Rich absorption oil withdrawn from scrubber 208 through line 212 is heated in exchangers 214 and 215, with the heated rich absorption oil in line 224 being introduced into a stripper 217, which includes suitable gas-liquid contacting means such as a bed 218. The stripper 217 is preferably provided with a stripping gas, such as steam through line 219, although, as hereinabove described, other stripping gases may be employed or the stripper 217 may be operated without a stripping gas or replaced with a flash drum. The stripper 217 is operated at conditions to strip absorbed aromatics from the absorption oil, with the stripped aromatics being withdrawn from the stripper 217 through line 221 for introduction into the cooling section 15 as hereinabove described with respect to FIG. 1, or in the alternative condensed separately. In general, stripper 217 is operated at temperatures in the order of from 125° F. to 300° F., and at a pressure in the order of from 1 to 25 psia.

Lean absorption oil is withdrawn from stripper 217 through line 222 and a portion thereof is purged through line 223. The lean absorption oil is cooled in exchanger 214 by indirect heat transfer with the rich absorption oil in line 212, and is further cooled in exchanger 230 prior to introduction into the absorption column 208 through line 211. Make-up absorption oil is provided through line 216.

Thus, in accordance with the embodiment of FIG. 3, prior to the final treatment with the heavier absorption oil, and subsequent to ethylbenzene scrubbing, the gas is cooled to condense additional aromatics therefrom.

Although the invention has been particularly described with respect to embodiments thereof as illustrated in the accompanying drawings, it is to be understood that the invention may be practised other than as particularly described with respect to the embodiments. Thus, for example, the various heat transfer stages may be effected other than as particularly described.

These and other modifications should be apparent to those skilled in the art from the teachings herein.

The present invention is particularly advantageous in that it is possible to recover essentially all of the aromatics which are present in the off-gas generated in a styrene production process. The increased recovery of aromatics improves the economics of the process. In addition, if hydrogen is to be recovered from the off-gas, by increasing the hydrogen concentration, such hydrogen recovery is enhanced.

These and other advantages should be apparent to those skilled in the art from the teachings herein.

Numerous modifications and variations of the present invention are possible in light of the above teachings and, therefore, within the scope of the appended claims, the invention may be practised otherwise than as particularly described.

We claim:

1. In a process for treating an off-gas generated in a process for producing styrene from ethylbenzene, said off-gas containing hydrogen and aromatic hydrocarbons, the improvement comprising:
   finally treating the off-gas, which comprises hydrogen ethylbenzene and a member selected from the group consisting of styrene, benzene, toluene and mixtures thereof, and which contains from 0.5% to 10% by volume of aromatic hydrocarbons by contacting the off-gas at a temperature of from 35° F. to 125° F. and a pressure of from 15 to 100 psia with an absorption oil for aromatics having a 5-volume percent distillation temperature of at least 400° F. to absorb aromatic hydrocarbons present in the off-gas and provide a remaining off-gas essentially free of aromatic hydrocarbons, which off-gas contains less than 0.2% by volume of aromatic hydrocarbons, wherein said absorption oil is a heavy byproduct from the production of ethylbenzene by alkylation of benzene, and which contains diphenylethane and polyethylbenzenes; and recovering aromatic hydrocarbons absorbed by said absorption oil by stripping.

2. The process of claim 1 wherein prior to the final treatment the off-gas is scrubbed with ethylbenzene to reduce the aromatic content of the off-gas.

3. The process of claim 1 wherein prior to the final treatment, the off-gas is chilled to recover aromatics by condensation.

4. The process of claim 1 wherein prior to the final treatment, the off-gas is scrubbed with ethylbenzene and chilled to reduce the aromatic content thereof.

5. The process of claim 1 wherein the absorption oil has a 5-volume percent distillation temperature of at least 600° F.

* * * * *